United States Patent [19]

Holbrook

[11] Patent Number: 5,403,741
[45] Date of Patent: Apr. 4, 1995

[54] APPARATUS AND METHODS FOR MICROORGANISM CULTURE AND TESTING

[75] Inventor: Roy Holbrook, Sharnbrook, England

[73] Assignee: Unilever Patent Holdings, B.V., Rotterdam, Netherlands

[21] Appl. No.: 997,134

[22] Filed: Dec. 22, 1992

Related U.S. Application Data

[63] Continuation of Ser. No. 567,693, Aug. 15, 1990, abandoned, which is a continuation of Ser. No. 384,094, Jul. 24, 1989, abandoned, which is a continuation of Ser. No. 90,478, Aug. 28, 1987, abandoned.

[30] Foreign Application Priority Data

Aug. 28, 1986 [GB] United Kingdom .................. 8620785
Jul. 7, 1987 [GB] United Kingdom .................. 8715978

[51] Int. Cl.$^6$ .......................... C12M 1/34; C12M 1/24
[52] U.S. Cl. ...................................... 435/291; 435/296; 435/300; 435/311; 435/810; 435/30; 435/34
[58] Field of Search ............... 435/29, 30, 34, 38, 435/252.1, 252.4, 253.1, 252.8, 253.6, 291, 299–301, 296, 809, 810, 292–294, 311; 422/99, 101, 102

[56] References Cited

U.S. PATENT DOCUMENTS

| 3,563,859 | 2/1971 | Fink | 435/294 |
|---|---|---|---|
| 3,817,839 | 6/1974 | Warren | 435/294 |
| 4,308,347 | 12/1981 | Forrer et al. | 435/34 |
| 4,920,063 | 4/1990 | Ward, Jr. | 435/34 |

OTHER PUBLICATIONS

Abrahamsson et al "Detection of Samonella by a Single-Culture Technique", Applied Microbiology, vol. 16, No. 11, pp. 1695–1698 (Nov. 1968).
Banwart et al "Rapid Determination of Salmonella in Samples of Egg Noodles, Cake Mixes, and Candies", Applied Microbiology, vol. 18, No. 5, pp. 838–842 (Nov. 1969).
Fung et al "A Rapid and Simple Method for the Detection and Isolation of Salmonella from Mixed Cultures and Poultry Products", Poultry Sci., vol. 49, pp. 46–54 (1970).
Chau et al "A Simple Procedure for Screening of Salmonellae Using a Semi-Solid Enrichment and Semi--Solid Indicator Medium", J. of Applied Bacteriology, 41:283–294 (1976).
Stuart et al "Isolation of Salmonellae by Selective Motility Systems", Applied Microbiology, vol. 13, No. 3, pp. 365–372 (May, 1965).
DeSmedt et al "Rapid Salmonella Detection in Foods by Motility Enrichment On a Modified Semi-Solid Rappaport-Vassiliadis Medium", J. of Food Protection, vol. 49, No. 7, pp. 510–514 (Jul. 1986).

*Primary Examiner*—William H. Beisner
*Attorney, Agent, or Firm*—Cushman Darby & Cushman

[57] ABSTRACT

Processes and apparatus are provided for selectively culturing motile bacteria such as Salmonella, Camplylobacter, and others. One embodiment entails providing a carrier partly dipping into the liquid nutrient medium but projecting above a surface of the liquid nutrient medium, the carrier containing supported (e.g. gelled) nutrient medium and having an opening below the surface of the liquid nutrient medium for contact between the liquid medium in the culture vessel and the supported medium of the carrier. Migration of the motile bacteria from the liquid into the supported medium during the culture is thereby facilitated. The sample and the nutrient media are incubated to allow growth of any motile bacteria present in the sample in the liquid medium, and to allow migration of the motile bacteria during the culture into the supported medium.

4 Claims, 4 Drawing Sheets

APPARATUS AND METHODS FOR MICROORGANISM CULTURE AND TESTING

This is a continuation of application Ser. No. 07/567,693, filed on Aug. 15, 1990, which was abandoned upon the filing hereof, and which is a continuation of application Ser. No. 07/384,094, filed Jul. 24, 1989, now abandoned, and which is a continuation of application Ser. No. 07/090,478, filed Aug. 28, 1987, now abandoned.

BACKGROUND OF THE INVENTION

1. Field of the Invention

This invention relates to apparatus and methods for micro-organism culture and testing. In particular embodiments it relates to devices and methods suitable for application to motile bacteria such as species, strains, and serotypes of Salmonella, Campylobacter, Listeria, Vibrio, Aeromonas, or Escherichia.

These examples of motile bacteria are particularly important subjects of culture and testing methods adapted to the surveillance of food hygiene, environmental hygiene and pollution, arid clinical samples, owing to their pathogenic nature in humans and animals.

2. Description of Related Art

Current methods are protracted and laborious, especially for example those methods often used to test for Salmonella contamination in food samples.

One standard method of testing for Salmonella contamination, e.g. in a food sample, involves the steps or:

(a) dispersing a 25 g sample of food or other material to be tested in 225 ml of a 'pre-enrichment' or 'resuscitation' medium comprising for example bacteriological peptone, and incubating for up to one day (e.g. at 37 deg. C. for 18–24 hours):

(b) subculturing the initial culture into each one of one or more different formulations (for example two) of 'selective enrichment' medium to depress the growth of other micro-organisms relative to that of any Salmonella present, and growing these enrichment cultures by incubation to yield a demonstrable population of Salmonella (if present): (the least demonstrable population level can be very variable, but can be for example about 1000 organisms per ml in the absence of other contaminants, otherwise maybe up to about a million organisms per ml or more in the presence of heavy contamination with other organisms):

(c) using the enriched cultures obtained to provide inocula for a series of selective differential solid growth media, usually on agar, in dishes allowing the identification of colonies of Salmonella if present in the original sample:

(d) conducting at least biochemical and/or immunological (agglutination) tests on any colonies provisionally identified as Salmonella to confirm or contradict the identification.

The whole process can take about a week.

Recently, improved immunological test methods have been developed which can substitute for parts (c) and (d) of the standard procedure and somewhat shorten the overall time taken.

The prior art also includes a technique proposed for the isolation of Salmonella by a selective motility system (P F Stuart and H Pivnick (1965), Applied Microbiology 13(3) pp 365–372). This involved the use of 'semisolid' gel media contained in U-tubes, from one side-arm of which bacteria were to be harvested after inoculation at the other side-arm using a sample from a pre-enrichment culture as inoculum at the surface of the semisolid gel.

A further technique depending on the motility of the organisms to be detected is contained in U.S. Pat. No. 4,563,418 (Bio-Controls, Inc.). This describes a motility-immunoimmobilisation method for detection of motile organisms such as Salmonella, and discloses a motility vessel with an opening at each end, with a cad to cover each end opening, and containing a gelled motility medium. The system is used by placing antisera to immobilise Salmonella in contact with the gelled medium at one end, and placing a selective enrichment medium containing chemotactic attractant such as L-serine together with an inoculum of the organisms from a prior selective enrichment culture in contact with the gelled medium at the other end. A positive result after incubation is indicated by a band of immobilised bacteria near that end of the tube where the antisera were added.

A further review and description of Salmonella detection including the topic of motility enrichment has recently been published by J M De Smedt, R F Bolderdijk, H F Rappold and D Lautenschlaeger (1986) J. Food Protection vol 49 (7) pp 510–514, and mentions transferring inocula from pre-enrichment cultures to form spots on the surface of semisolid agar containing Rappaport-Vassiliadis broth: after 24 h incubation, samples from the edges of areas where migrated bacteria appeared to have grown were further subcultured and tested for presence of Salmonella.

U.S. Pat. No. 3,704,204 (Armour & Co) describes an attempt to achieve rapid testing for Salmonella, exemplified by incubating samples of meat and bone meal in nutrient media containing selective inhibitory agents, represented by bile salts, deoxycholate, lithium chloride and an acridine derivative (acriflavin), with a cotton swab saturated with lead acetate placed approximately an inch and a half above the surface of the medium: blackening of the swab after 24 h incubation was taken as a positive (suspicious) result. Numerous false positives were reported to be given by this method, though no false negatives.

In spite of these efforts, it still remains a problem, however, to shorten this process of testing for motile bacteria in a convenient way, particularly in respect of the earlier stages of culture also.

SUMMARY OF THE INVENTION

One aim of the present invention is to provide devices and methods for testing for motile bacteria which enable a test result to a good standard of reliability to be obtained from culture of a sample in a single vessel.

Another aim of the invention is to provide convenient devices and methods for selective enrichment culture and testing of motile bacteria to simplify and/or reduce the handling of samples and cultures required by the operator.

In one aspect, the invention provides a process for selectively culturing motile bacteria, comprising the steps of:

(a) preparing for bacteriological incubation a sample of material suspected of containing motile bacteria, (b) placing said material into a culture vessel containing liquid nutrient medium suitable for resuscitation and growth of motile bacteria, (c) providing a carrier partly dipping into said liquid nutrient medium but projecting above a surface of said liquid nutrient medium, said carrier containing supported nutrient medium selected from media suitable for bacteriologically selective growth and indication of motile bacteria, said carrier having an opening below said surface of said liquid nutrient medium for contact between said liquid medium in said vessel and said supported medium in said carrier, thereby to allow migration of said motile bacteria from said liquid into said supported medium during the culture, and (d) incubating said sample and said nutrient media to allow growth of any motile bacteria present in said sample in said liquid medium, and to allow migration of said motile bacteria during the culture into said supported medium and growth of said motile bacteria therein.

In several embodiments of the process, said carrier can also have an opening above said surface of said liquid nutrient medium, and said supported nutrient medium a transfer surface accessible for transfer of a sample of said bacteria after their migration into said supported medium and growth and migration therethrough, and said process can comprise the further step of transferring said motile bacteria from said transfer surface of said supported medium after growth of said bacteria into and through said supported medium.

According to another aspect of the invention there is provided apparatus for selectively culturing motile bacteria, said apparatus comprising:

(a) a culture vessel containing liquid nutrient medium suitable for resuscitation and growth of motile bacteria, and (b) a carrier partly dipping into said liquid nutrient medium and projecting above surface of said liquid nutrient medium, said carrier containing supported nutrient medium selected from media suitable for bacteriologically selective growth and indication of motile bacteria, said carrier having an opening below said surface of said liquid nutrient medium for contact between said liquid medium in said vessel and said supported medium in said carrier, thereby to allow migration of said motile bacteria from said liquid into said supported medium during culture of said bacteria.

The invention thus enables the culture, selection, enrichment, and in many examples also the detection of micro-organisms, e.g. motile bacteria. The invention can use per-se known forms of liquid medium for the resuscitation and growth of the micro-organisms to be tested for, and includes the provision of dry ingredients to form such medium upon rehydration with water or with a suitable basal medium. Similarly, there can be used per-se known forms of supported selective enrichment medium selective for the micro-organisms to be tested for, and/or indicator media for indicating presence and growth of the micro-organisms to be tested for, and variants thereof, including dry preparations to form such a supported medium upon rehydration with water or with a suitable basal medium.

Also provided by the invention are carriers of supported media incorporating features as described below, and for use in culture procedures as described herein.

In the use of the invention, the culture container and the supported medium are located so that the selective enrichment and/or indicator medium is in a zone or container in contact with the resuscitation and growth medium, whereby in use the micro-organisms to be tested for can grow or migrate preferentially into the enrichment medium during the culture itself, and do not require to be transferred by manual inoculation.

In this specification 'supported medium' means a liquid growth medium associated (e.g. interspersed) with a gel or solid material to such an extent that convection is substantially prevented but motile organisms are not prevented from migrating therethrough, nor (in an appropriate case) non-motile organisms prevented from growing therethrough. This condition can be supplied for example by a medium including a gelling agent, or by a liquid medium supported e.g. by a solid network or framework to such an extent that convection is substantially prevented. Suitable examples of supports, without limitation, are weak gel materials such as 'sloppy' gels known per se for enrichment of motile bacteria, and fibrous conductive material, such as filter papers and nylon or polyamide or polyester filters, especially pleated filters which define very narrow longitudinal channels containing liquid or semisolid gel along which micro-organisms can grow, or can travel by their own motile properties, or porous polymer filters.

Selective media and enrichment media are understood as culture media containing selectively inhibitory agents chosen to prevent or reduce growth of most micro-organisms other than the micro-organism under test, while being at worst only mildly inhibitory, and preferably neutral or stimulatory towards the growth of the wanted micro- organisms. Examples of such agents and their dosage are well known in the art and do not constitute this invention. In the case of Salmonella, known selective agents include bile salts, acridine derivatives and certain other ingredients of media described below, e.g. dyes such as brilliant green.

The liquid resuscitation/growth media used in this invention can be free of selective inhibitors. For salmonella testing, selective inhibitors such as malachite green are advantageous. The resuscitation/growth media should in most cases be free of chemotactic attractants so as to allow known chemotactic attractant(s) such as L-serine to be selectively included if desired in the supported medium, thereby to enhance the (auto-)transfer of the motile micro-organisms from the liquid resuscitation medium into the supported selective and/or indicator medium.

The invention enables a food or other specimen to be added to the culture device, to produce after a single incubation stage an enriched culture of any of the micro-organisms to be tested for (if present).

One of the advantages of the present invention is that by its use one can provide a culture device which can allow an adequately dense and enriched culture of a motile species of bacteria such as Salmonella to be obtained on the basis of a single culture device inoculated with a food sample.

Also provided by the invention is a corresponding process for the selective enrichment culture of micro-organisms, e.g. bacteria, especially for example motile bacteria, comprising inoculating a liquid medium for the resuscitation and growth of the micro-organisms to be tested for, with a macerated food or other sample suspected of containing said micro-organisms, and allowing said micro-organisms if present to resuscitate and grow in said liquid medium, wherein said liquid medium is incubated in liquid contact with a supported selective enrichment medium for said micro-organisms, whereby any of said organisms if present are caused to grow or migrate into said selective medium during said incubation, thereby to yield at the end of said incubation a selectively enriched culture of any of said micro-organisms if present in said sample.

Also provided by the invention are materials for selective enrichment culture as described above, the materials comprising a set of prepared reagents and carriers including dry prepared reagents, to be rehydrated with water or a basal medium to provide devices and the inserts therefor carrying supported media, as described above. Such materials are preferably distributed in the form of sealed dry sterile packs to be opened and rehydrated when required for use.

In a device according to one embodiment of the present invention, the semi-solid or otherwise supported selective enrichment and/or indicator medium is supported in a second container, or second zone of the culture container, to allow a sample of enriched culture from the selective enrichment and/or indicator medium to be withdrawn conveniently at the end of a culture period.

The selective enrichment and/or indicator medium in the second container can if desired be separated from the liquid medium in the first container by a supporting partition such as a mesh, filter or porous membrane or other partition provided that any such partition is such as to allow the passage of motile bacteria therethrough. Suitable pore sizes are at least of the order of about 5 to 10 micron—larger pores are acceptable and advantageous. Suitable porous polymer material is e.g. "Porex" (Trade Mark) as sold by Porex Technologies Inc., and a presently preferred example of such material is that obtainable as Porex cat. X4898 fine grade hydrophilic DBS porous polymer of pore size 15 to 45 micron, e.g. as ⅛ inch thick sheet which can be cut to disks of appropriate size.

In one convenient arrangement for example there is a zone of liquid medium left in contact with the semi-solid selective enrichment or indicator medium, e.g. by slight syneresis of a gel included in the semi-solid enrichment medium to provide a convenient sampling point accessible to sampling via a sampling aperture of the second container or container zone. This can facilitate extraction of samples of the enriched culture in liquid form, which may be preferable to taking samples of semi-solid culture.

If desired, apparatus according to the invention can be provided with more than two zones of culture medium, arranged in a series so that any motile bacteria that migrate from the inoculation zone of liquid medium to the sampling point have to traverse more than two zones of culture medium. This arrangement can be put together for example with a secondary tube containing supported selective enrichment and/or indicator media. Such a tube can have for example an open top and bottom, and can dip into a liquid resuscitation culture medium, providing liquid contact between the liquid medium and the supported media within the tube via a macroporous membrane or filter or other partition which can be traversed by the organisms, at the lower end of the tube, and containing a plurality of gel or other supported layers of enrichment media with a sampling point accessible from an open upper part of the tube or other convenient sampling point.

The device can be used according to the invention by (a) inoculating a sample of material suspected of containing motile bacteria into the zone of liquid culture medium but not into the zone or zones of enrichment media (this can be done for example by comminuting or otherwise dispersing the sample with and into the liquid culture medium), (b) incubating the culture media to allow the motile bacteria (if any) to multiply and migrate into the zone or zones of enrichment media, and (c) sampling an enriched culture containing motile bacteria (if any were present in the inoculum) from the zone or one of the zones of enrichment medium.

A further embodiment of a culture apparatus according to the invention comprises two or more zones of semi-solid or otherwise supported selective and/or indicator media arranged in parallel so that the organisms e.g. motile bacteria which are sought may grow or migrate from the inoculation zone of liquid medium into each parallel zone, each comprising one or more semi-solid or supported selective/indicator media. This can be arranged for example with secondary tubes dipping into a liquid culture medium, providing contact between the liquid media and supported media via a microporous membrane, filter or other partition at the lower end of each tube and having a sampling point accessible from an open upper part of each tube.

This and other embodiments bring the advantage that in a single culture vessel two or more forms of selective enrichment and/or indicator culture for motile bacteria can be carried out at the same time and in many instances without manipulation after the initial inoculation.

The sample of enriched culture can then be tested for the presence of the organisms under investigation, e.g. the motile bacteria, by any suitable method, e.g. by microbiological culture, biochemical, immunological or microscopic test methods.

A preferred form of the materials, and correspondingly of the apparatus, of the invention, comprises a tubular carrier open at each of two ends and carrying a supported selective enrichment medium, or dry materials to be rehydrated to form said medium. Whether the supported medium is in the form of a gel or liquid, then it can be retained in the tubular carrier by means of a suitable porous retainer to allow passage of microorganisms therethrough. The retainer in the case of a liquid medium can for example be in the form of a relatively tightly pleated filter of paper or plastics material, which leaves longitudinal channels sufficiently narrow to prevent any substantial convection therethrough, but allows the growth or motile passage of the microorganisms to be tested for. It has been found possible to employ pleated filters of the kind conventionally used to make the filters of filter cigarettes.

The tubular carrier can conveniently be cylindrical but this is not essential and other cross-sectional shapes can be used. 'Tubular carrier' includes any shape with an open bottom and an open top or a top which communicates with other apparatus or material into which motile bacteria can migrate for further testing. In a convenient embodiment the tubular carrier can be of plastics water-impermeable material, and can contain one or a plurality of zones of similar or different selective enrichment and optionally also of diagnostic media suitable for the micro-organisms to be tested for, arranged in sequence so that a culture of organisms must traverse each zone in proceeding from one end to the other end of the tubular carrier.

Preferably the tubular carrier carries, at its open end which is remote from the open end which in use contacts the resuscitation medium, free liquid or a porous material from which a sample of free liquid can easily be extracted as a sample of enriched culture for the purpose of supplementary diagnostic or culture procedures if desired (e.g. by squeezing the tube). If there is more than one supported medium in the tubular carrier, then it can be useful to provide a vent for one or more of the compartments which are not open at the top, to allow escape of e.g. metabolic gases or air during rehydration.

Presently preferred non-limitative examples of media for use for example with test devices as described and illustrated below are formulated and used as follows.

(a) Medium 1 (medium suitable for the resuscitation and growth of salmonellae in an incubation tub) can usefully be made up in aliquots of dry powder sufficient when taken up in sterile water to yield 225 ml of the following composition:

Casein tryptone (Oxoid L42), 10 g/l; sodium chloride, 5 g/l; disodium hydrogen phosphate 3.5 g/l; potassium dihydrogen phosphate 1.5 g/l; malachite green (Merck bacteriological grade) 40 mg/l. This medium, when made up, should have a pH of about 7.2.

Medium 1 is preferred for the examination of samples in which little or no contamination is expected with microbes other than those related to Salmonella—e.g. milk and egg products such as dried milk and dried egg, etc.

An alternative medium 1a contains additionally 40 mg/l novobiocin and 4 g/l (antibiotic-free) non-fat dried milk powder. In a variant of this alternative, presently preferred for the clarity of the resulting medium, 3.0 g/l casein is substituted for the milk powder. This alternative medium is preferred for testing products in which much non-Salmonella contamination may be expected, e.g. meat products.

(b) Medium 2 (LID) (selective supported medium with indicator for growth and transfer of motile Salmonella) comprises a dry powder of a composition suitable to yield on rehydration a highly viscous medium of the following composition marked "Wet":

|  | Wet (g/l) |
|---|---|
| Bacteriological peptone (Oxoid L37) | 10 |
| Yeast extract (Oxoid L21) | 6 |
| Dextrose | 2 |
| L-lysine | 20 |
| Ferric ammonium citrate | 1 |
| Sodium thiosulphate | 0.08 |
| Sodium alginate | |
| (Alginate Industries/Kelco Manucol DMF) | 10 |
| (or - preferably - xanthan gum 3.75 g/l instead of alginate) | |
| L-serine | 1 |
| Sodium desoxycholate | 5 |
| (Final pH about 6.7) | |

Medium 2 can be dosed as an aliquot of dry powder into the lower chamber of a carrier tube. A presently preferred variant of medium 2 (LID) contains 3.75 g/l xanthan gum and 1.25 g/l lactose instead of the sodium alginate.

(c) Medium 3 (modified RV: based on Rappaport-Vassiliadis Medium) is an alternative selective supported medium with indicator, for growth and transfer of motile salmonellae) comprises a dry powder suitable to yield on rehydration a highly viscous medium of the following composition "Wet":

|  | Wet (g/l) |
|---|---|
| Soya peptone, neutralised (Oxoid L44) | 5 |
| Sodium chloride | 8 |
| Potassium dihydrogen phosphate | 1.6 |
| Magnesium Chloride (anhydrous) | 18.7 |
| Sodium alginate | |
| (Alginate Industries/Kelco Manucol DMF) | 12.5 |
| Serine | 1 |
| Malachite Green (bacteriological grade) | 0.04 |
| (final pH about 5.2) | |

Medium 3 is also intended here for use for example in the lower chamber of a tube carrier.

(d) Medium 4 (BGD) (brilliant green desoxycholate indicator medium):

|  | Wet (g/l) |
|---|---|
| Lab Lemco Powder (Oxoid) | 5 |
| Bacteriological peptone (Oxoid) | 10 |
| Yeast extract (Oxoid L21) | 3 |
| Lactose | 10 |
| Sucrose | 10 |
| Disodium hydrogen phosphate | 1 |
| Sodium dihydrogen phosphate | 0.6 |
| Phenol red | 0.09 |
| Brilliant Green | 0.0047 |
| L-serine | 1 |
| Sodium desoxycholate | 5 |
| Sodium alginate (Manucol DMF) | 10 |
| (or - preferably - xanthan gum 1 g/l instead of alginate) | |
| (final pH about 6.9) | |

Medium 4 is intended here for use for example in the upper part of a tube carrier.

(e) Medium 5 (LICNR) ('lysine iron cystine neutral red' indicator medium):

|  | Wet (g/l) |
|---|---|
| L-lysine monohydrochloride | 8 |
| L-lysine dihydrochloride | 2 |
| Tryptone (Oxoid L42) | 5 |
| Yeast extract (Oxoid L21) | 3 |
| Lactose | 5 |
| Glucose | 1 |
| Salicin | 1 |
| Ferric ammonium citrate | 0.5 |
| Sodium thiosulphate | 0.1 |
| L-cystine | 0.1 |
| L-serine | 1 |
| Sodium alginate (Manucol DMF) | 7.5 to 10 |
| Neutral red | 0.025 |
| (final pH about 6.2) | |

This medium is also intended here for use for example in the upper part of a tube carrier.

In one useful way of using these media, a first selective indicator tube with two compartments may contain, in the lower compartment, medium LID, and in an upper compartment medium BGD, and a second, parallel constructionally similar selective indicator tube can have, in the lower compartment, modified RV medium, and in the upper compartment, LICNR medium.

A useful general feature of these examples of media is that the one or more selective/indicator media are (weakly) gelled and contain a chemotactically effective amount of serine or other bacteriological chemotactic attractant, while the resuscitation/growth medium is liquid and lacks any added serine or other such attractant.

BRIEF DESCRIPTION OF THE DRAWINGS

Certain embodiments of the invention are further described with reference to the accompanying drawings given by way of non-limitative example.

Referring to the accompanying diagrammatic drawings, not to scale:

FIG. 1 is a diagrammatic perspective view of a unit array of microbiological test devices according to an embodiment of the invention.

FIG. 2 is a diagrammatic perspective view of a test device forming part of the array of FIG. 1.

FIG. 3 shows a diagrammatic plan and horizontal part-section through the device of FIG. 2.

FIG. 4 shows a diagrammatic side part-sectional view of the device of FIG. 2, and FIG. 5 shows diagrammatically the construction of a tubular carrier as in FIG. 1.

Except where otherwise indicated, in this description the culture media referred to and their ingredients can be as described in the Oxoid Manual, published by Oxoid Ltd, Wade Road, Basingstoke, Hampshire RG24 0PW, UK (5th edition, 1982) and in its updating appendices.

DESCRIPTION OF THE PREFERRED EMBODIMENTS

Figure 1:
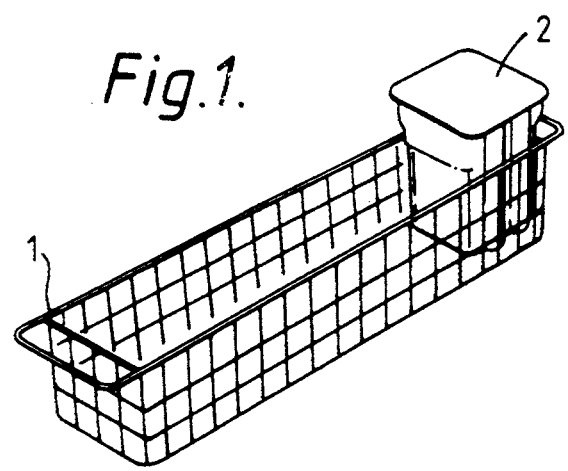
FIGS. 1, 2, 3, 4 and 5 represent a preferred embodiment of the invention by way of example only.

Referring to FIG. 1, a holder 1 in the form of a wire basket is shown, holding a test device 2 which has outwardly the form of a thermoformed plastics with lid. Holder 1 has a capacity to hold an array of test devices like test device 2, in this case as a row of devices.

Figure 2:
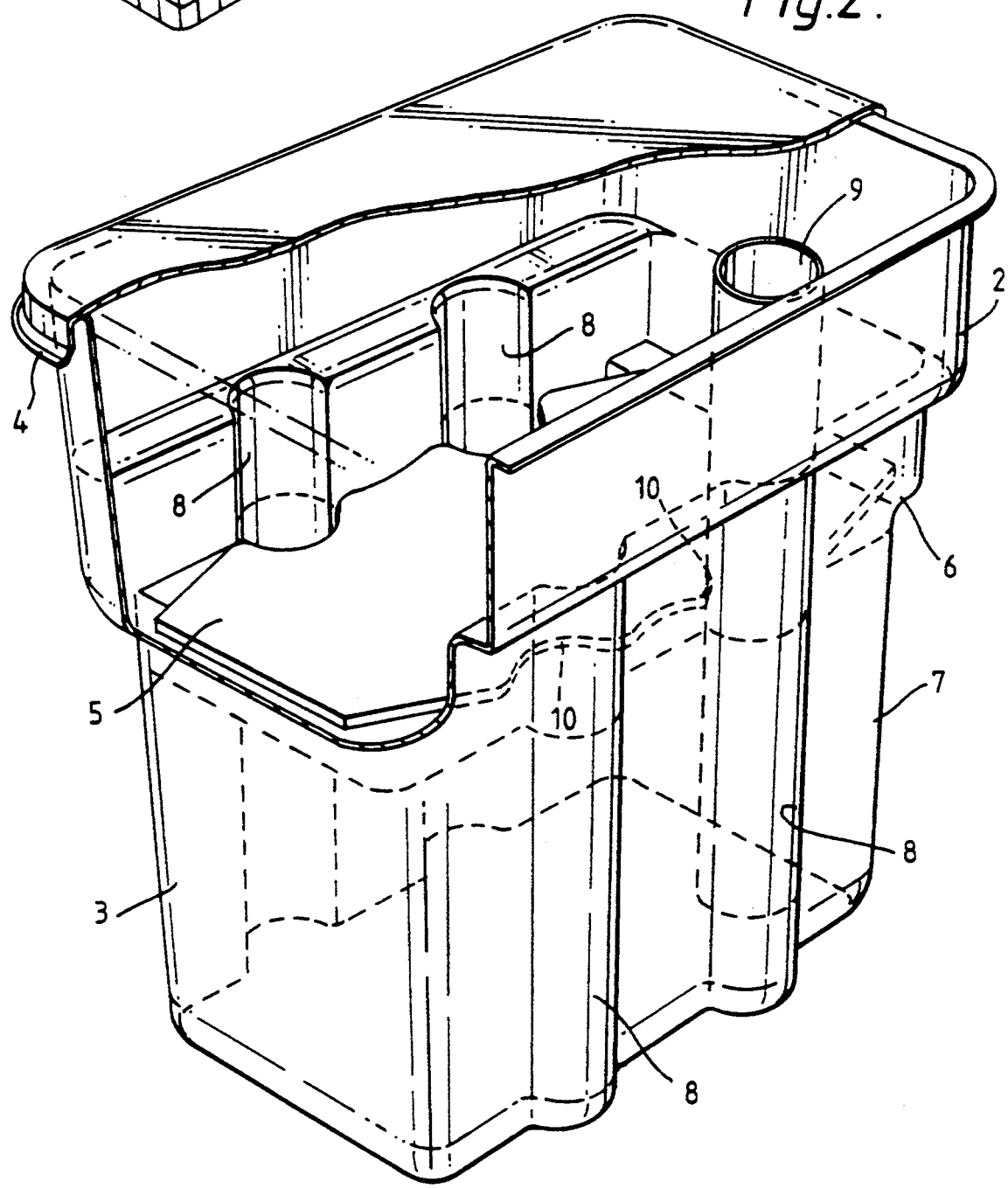

FIG. 2 shows in part-sectional perspective form a diagram of a test device 2 like test device 2 of FIG. 1. Test device 2 comprises a thermoformed plastics tub body 3 provided with an overall flanged lid 4 and an internal removable plastics cover 5 which in use sits on a ledge 6 formed in body 3 to support cover 5. In the example, plastics body 3 has substantially transparent sidewalls, and is in fact made throughout of substantially transparent plastics material. A lower part 7 of device body 3, below cover 5 and ledge 6, is formed as an incubation container for a microbial growth medium and test sample to be described below. In one useful form, device 2 is dimensioned to accommodate conveniently about 250 ml of liquid and sample (together with convenient headspace) below internal cover 5.

Formed in sidewalls of device body 3 are locations 8 to receive and hold carriers for supported microbiological media. Four such locations 8 are shown in FIG. 2. These locations 8 take the form of half-cylindrical recesses to receive and hold tubular carriers like one such carrier shown as 9 in FIG. 2. Tubular carrier 9 is held in place in the device of FIG. 2 by the combined action of location 8 in the flexible sidewall of body 3 and a substantially semicircular recess like recess 10 in internal cover 5. Body 3 and cover 5, being slightly flexible, allow for easy insertion and removal of the tubular carriers like 9. Up to four such carriers can be accommodated in each of the tub bodies 3.

Figure 3:
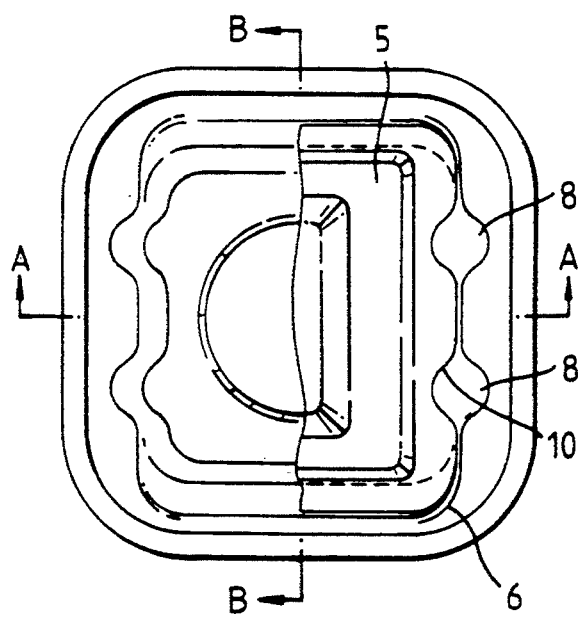
Figure 4:
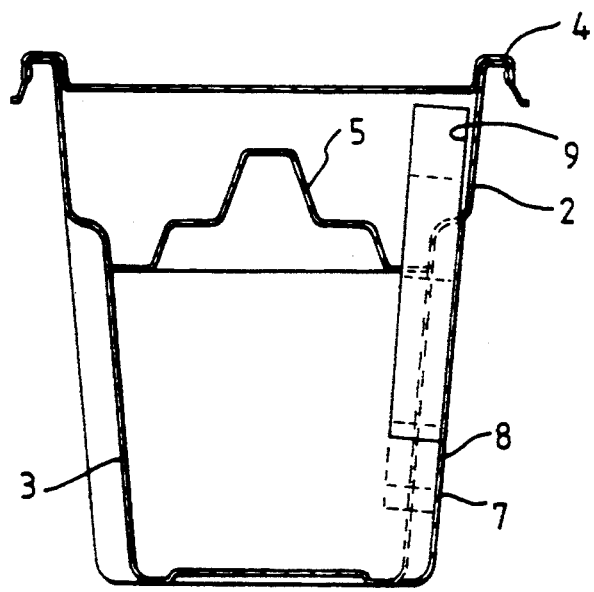

Further detail of the construction of the tub bodies 3 and lids 4 and internal covers 5 are shown in FIGS. 3 and 4.

Figure 5:
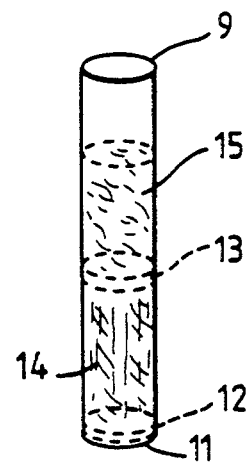

Construction of the tubular carrier 9 is shown in FIG. 5.

Each tubular carrier 9 (e.g. of polystyrene, which can be somewhat flexible) has an open top and an open bottom 11, and for example at least two porous partitions 12, 13, (e.g. of Porex DBS hyrophilic porous polymer sheet as described herein) which divide its interior into a plural number of compartments 14, 15. The uppermost 15 of the compartments can be open or topped by a further porous partition. The partitions are of course arranged so that the carriers can be used in the manner described herein, i.e. so that when they are dipped in a liquid medium the liquid medium can contact the medium contained within the carriers: for this purpose the lowermost partition is normally at or close to the bottom of the tube.

Suitable dimensions for polystyrene tube 9 and its fitments are for example: internal diameter about 9 mm, lower chamber volume (e.g. for selective medium) about 1 ml, height and volume of upper medium about 8 mm and 0.6 ml, overall height of tube about 65 mm.

Contained within each mentioned compartment is a culture medium selective for motile bacteria and/or capable of indicating the growth of motile bacteria therein.

Suitable media include for example those described above. Serine is an especially useful medium component for rendering the media chemotactically attractive to some motile bacteria, e.g. salmonella and escherichia.

The material for the partitions can be for example Porex (Trade Mark) porous polymer made by Porex Technologies Inc., especially for example hydrophilic DBS polymer sheet about ⅛ inch thick, cut to form disks about 1–3 mm, preferably more than 2 mm, thick. Where a dry medium is used and rehydrated by contact with water, it can be preferable to give the polymer disks a light coating of hydrophobic material on their lower side (e.g. "Repelcote", Trade Mark). The medium is introduced into the compartments in the form of dry powder which is rehydratable to form a gel. The lactose and alginate ingredients (or presently-preferred xanthan and lactose ingredients) in the media mentioned above, together with the hydrophobic lower surface of the porous disks, have been found in certain cases to promote smooth water uptake to form continuous gel media communicating with each other via aqueous-liquid-filled porous partitions in the tubes.

The tubes are normally made up with dry powdered media components and sterilised in sealed e.g. foil packs by x-irradiation.

The apparatus may be used for example as follows.

Preparation of the sample for the incubation can conveniently be achieved for example by dispersing the sample in the medium by means of a Stomacher (Trade Mark) homogeniser device (available from Seward Surgical, UAC House, Blackfriars Road, London SE1), (or otherwise as described in U.S. Pat. No. 3,819,158/GB 1 402 538).

It can be convenient to use sample and medium in proportions about 25 g to 225 ml respectively. (However, it is within the scope of the invention in this and other cases to use larger scales of material and to group and mix a number (e.g. up to about 10) of samples, e.g. samples each of about 25 g, for testing as a single effective sample in the manner described herein. Naturally, if such a grouped sample turns out positive, suspicion is cast on each of the individual sources from which the group was made, and further testing is needed.)

The sample and liquid nutrient medium can then be placed in the culture vessel together with one or more tube carriers loaded with appropriate media as described above, with the supported media in contact with the medium in the culture vessel. The tube carriers are preferably located so that their lower ends dip below the surface of the liquid nutrient medium with their upper ends projecting above the liquid level.

After incubation, e.g. at 37 deg. C., or up to 41.5 deg. C. e.g. for 18-24 hours, or up to about 48 hours if needed, the presence of salmonellae may be shown by blackening of any zone with lysine-iron broth, and/or colour change of any zone of brilliant green indicator broth to red, or by corresponding colour change of per-se known type in the case of alternative indicator media used, e.g. alternatives as described herein.

A liquid sample of enriched Salmonella culture can be removed if desired for confirmatory culture and/or testing from the open top 9, if necessary by slightly squeezing the flexible tube containing the supported medium to release culture liquid from the gel or other form of supported medium. The culture device may be incubated longer if desired.

After a suitable culture period it is possible to remove a convenient sample drop of liquid located at the upper surface of the supported media in the tube carrier if desired as a sample enriched in the motile bacteria to be detected. Generally, where an array of culture vessels is set up to test a multiplicity of samples, it will only be necessary to withdraw samples for further testing from those tubes showing a positive indicator reaction. It is within the scope of the invention to incorporate means for further testing to communicate with the top of the tube carriers containing selective/indicator media.

Figure 6:
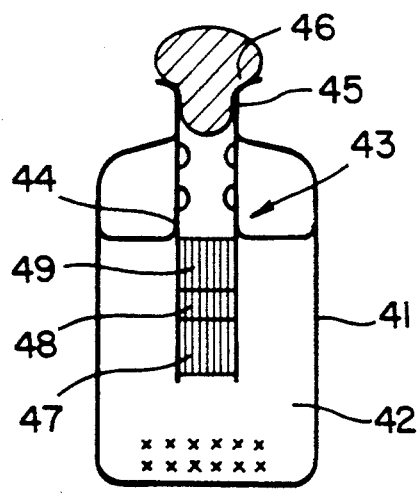
FIG. 6 shows in section a culture apparatus according to an alternative embodiment of the invention.

Referring to FIG. 6, there is shown an alternative device comprising a culture bottle 41 containing bacteriological peptone—water medium 42 to act as a resuscitation and growth medium containing dispersed therein a suitable quantity of the food or other material to be tested for micro-organisms. This example is directed towards testing the sample for contamination with Salmonella. Sample preparation and incubation in this case can be substantially as described in respect of FIG. 1 to 5.

Culture bottle 41 also contains a carrier insert 43, which provides a second zone of the culture container formed here by bottle 41, which second zone can be fixed in relation to the aperture of the culture container: in this example insert 43 carries one or more selective enrichment and/or indicator media selective for Salmonella in supported form such that the organisms can migrate into the carrier insert 43 and the medium therein and are selectively enriched and/or indicated by the nutrient media located therein, while at the same time the passage or growth of other organisms thereinto is not encouraged.

Carrier insert 43 comprises a flexible water-impermeable plastics tube 44, suspended and mounted from aperture 45 of culture bottle 41, which is closed with a porous bacteriological plug 46. Tube 44 has open top and bottom ends, and in this example it also has a number of lateral apertures above the liquid level to allow air exchange.

Carried within tube 44 are three zones of medium each supported by a close-packed pleated filter similar to the type used to make the filters of filter cigarettes. The pleated filters leave longitudinal narrow channels which run substantially parallel to the axis of tube 44. Each of three pleated filters 47, 48 and 49 forms a plug supported within tube 44. The filters touch or nearly touch each other. Filters 47 and 49 are paper filters impregnated with media as described below. Filter 48 is of paper or plastics material and contains liquid which has flowed in with whatever media constituents it may carry when the assembly of tube 44 with filters 47, 48 and 49 was rehydrated from a dry impregnated state with water or with nutrient medium.

Plug 47 in this example is rehydrated from dry material impregnated with ingredients to make lysine-iron broth. (The agar, xanthan or other gelling ingredient normally included in such broth may be either present or absent). Plug 49 in this example is rehydrated from dry material with ingredients to make brilliant-green indicator broth. Gelling ingredient may be present or absent.

Tube 44 and its filter plugs 47, 48 and 49 within can be rehydrated before use by wetting in sterile distilled water for about 5 minutes, then aseptically transferred and inserted into bottle 41 in the position shown in FIG. 1.

The use of this device, like the use of other embodiments of devices and methods according to the invention, means that the number of subculturing or extra testing manipulations can be reduced to those needed for the (possibly few) bottles showing positive signs in an array of bottles, deriving from several suspect samples. The device, like many alternative forms of the invention, also enables a speedy culture test result to be obtained.

Figure 7:
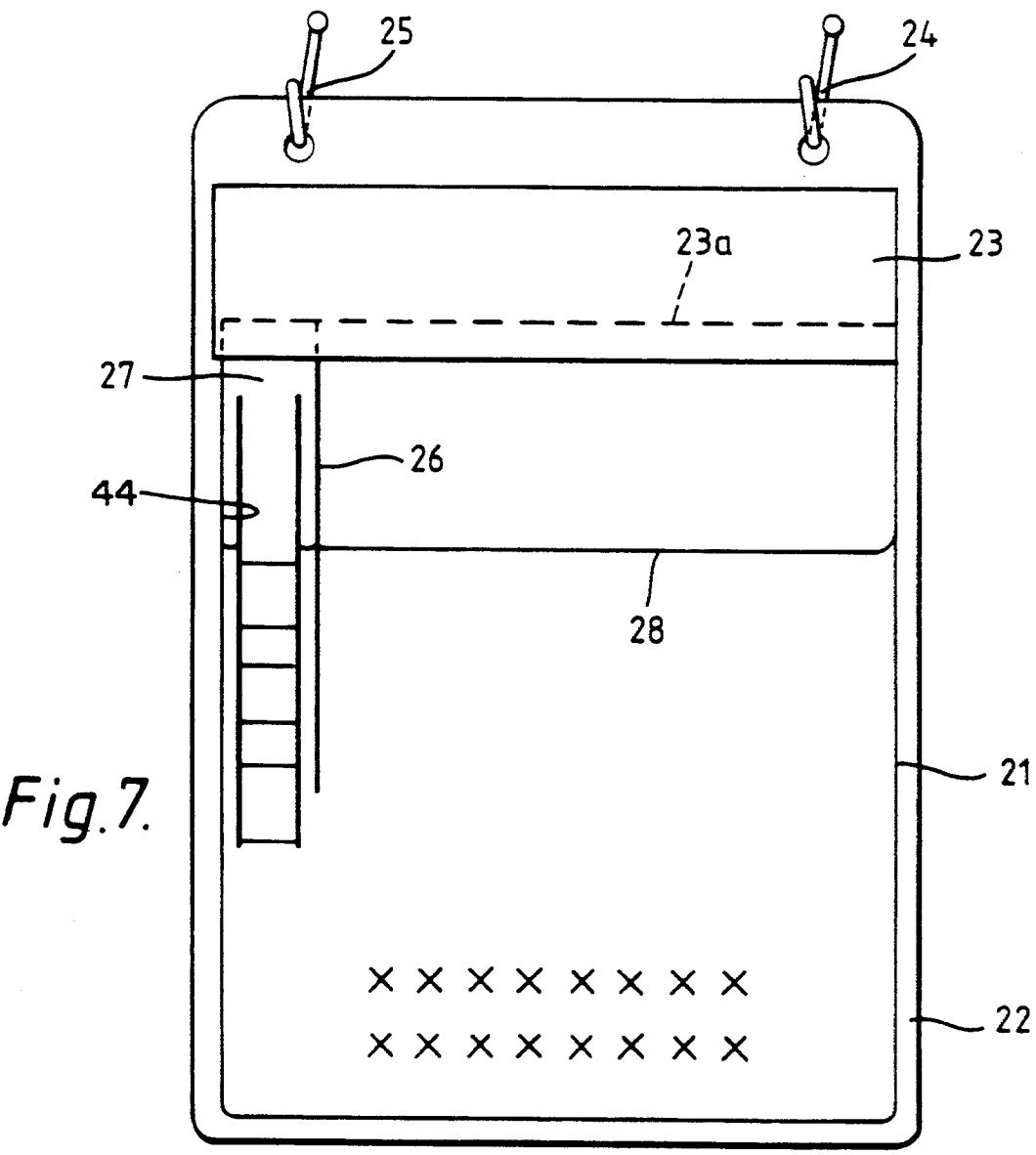
FIG. 7 shows in diagrammatic front view a further alternative form of culture apparatus.

Referring to FIG. 7, (not to scale), arrangements are shown which are analogous to those of FIG. 1 except as follows.

In place of bottle 1 there is provided a flexible plastics bag 21 made primarily of two sheets heat-sealed at their margins 22 to form a bag to contain culture medium for resuscitation and growth of the micro-organisms. A flap 23 covers the aperture formed by a rear sheet of the bag and the upper margin of a front sheet 23a. The bag can be suspended in use by two hangers 24, 25, and by a stiff support extending between the two hangers. A further heat-sealed seam 26 divides the bag into a main compartment and a side pocket 27 to receive and hold an impermeable flexible plastics tube 44 open at top and bottom and supporting selective enrichment and/or indicator media substantially as described for FIG. 6. Side pocket 27 is in communication below with the main compartment for culture medium, of which the surface is shown at 28, because seam 26 does not extend fully to the bottom of the bag.

Tube 44 and its contents are analogous to those described for FIG. 6 except that it contains 5 plugs made from packed pleated filter material.

The lowermost plug is rehydrated from a dry preparation impregnated with ingredients to give double strength lysine-iron broth (apart from unnecessary gelling ingredients) so that sufficient colour reaction may be obtained even if some of this broth leaches out into the bulk growth and resuscitation medium. The middle plug contains (before rehydration) ingredients to give single strength lysine-iron broth and the uppermost plug contains (before rehydration) ingredients to give brilliant green indicator broth. In a suitable example the total length of all five plugs can be about two inches and their diameter about a quarter of an inch.

Use of the device can be as described for FIG. 7, mutatis mutandis.

Figure 8:
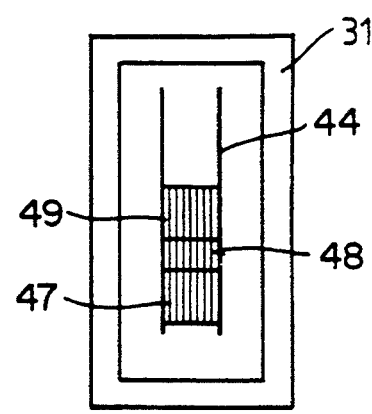
FIG. 8 shows in section a sterile sealed sachet containing a dry cylindrical support to be rehydrated and which can then form part of the apparatus shown in FIG. 6 or FIG. 7.

Referring to FIG. 8, there is shown a sterile sealed dry pack in accordance with an embodiment of the invention formed of a plastics envelope 31 containing dehydrated materials to form the tube 44 and supported media carried therein as described above. The dried (e.g. paper) plugs can be prepared by drying suitable quantities of material to form the media indicated above upon the plug material before it is pleated and packed, e.g. in vacuum at 60 deg. C. The materials can be sterilised after drying, pleating, packing in tube 4 and sealing in envelope 31, by means of gamma-irradiation at 0.5 Mrads (kGrays). Multiple inserts can be packed in each envelope 31 if desired, along with any desired quantity of desiccant if appropriate.

An important variation on the tube inserts as described for FIGS. 6–8 is constituted by the use of gel-supported semisolid media constrained by porous e.g. macroporous partitions, as for example described in connexion with FIGS. 1 to 5. These can be dry-packed as described for FIG. 8.

One suitable insert tube (not shown in the drawings) contains gelled medium based on ingredients as in Oxoid (Trade Mark) bismuth sulphite broth (3.016 g %) with sodium cholate (0.2 g %), sodium desoxycholate (0.6 g %), novobiocin (0.04 g %) and xanthan (0.4 g %). This mixture selectively cultures Salmonella and turns black in case of a positive result. The gel can be retained in the tube by means of a porous filter membrane fixed across the lower end of the tube. Such a membrane can of course also be used in connection with the embodiments using pleated filter supports.

In an alternative embodiment also in this case for Salmonella, a device for containing a selective enrichment medium, in the form of a gel, in liquid contact with a resuscitation and growth medium, can comprise an open thermoplastics tube of about 1 inch in diameter at its open bottom end, narrowing to about ¼ inch in diameter at its open top end, with an overall height about 1 inch. Fine nylon mesh membrane is sealed with adhesive around the edge of the bottom opening. Suitable mesh for this and other embodiments is mesh of 10 micron aperture size, 190 meshes per cm, made from 42 micron diameter nylon thread, the mesh having a water permeability of the order of 80 litre/sq. metre/sec, (commercially available as Simonyl HD10 (Trade Mark)), this device may be supported or caused to float on the surface of a resuscitation/growth medium, and contains selective enrichment medium as described above. The upper aperture can be used as a sampling port.

Figure 9:
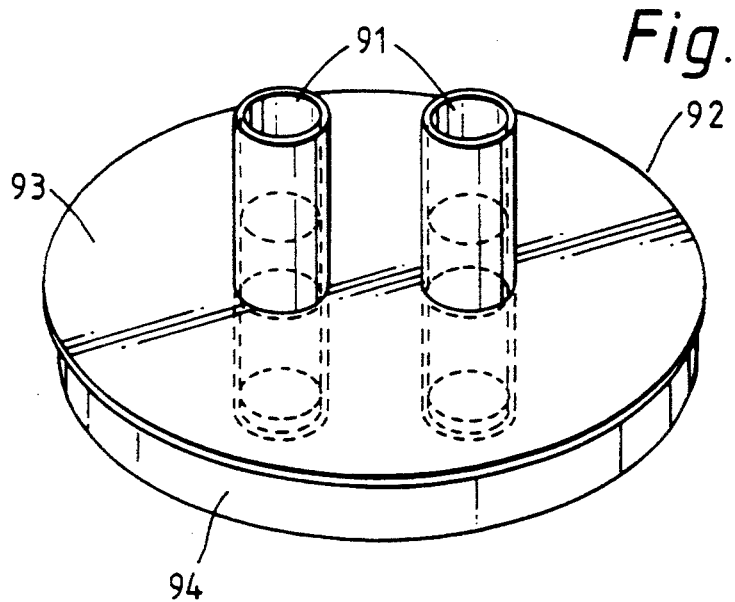
FIGS. 9 and 10 show in digrammatic perspective and vertical section tube carriers substantially as shown in earlier FIGS. held in a floatable holder.
Figure 10:
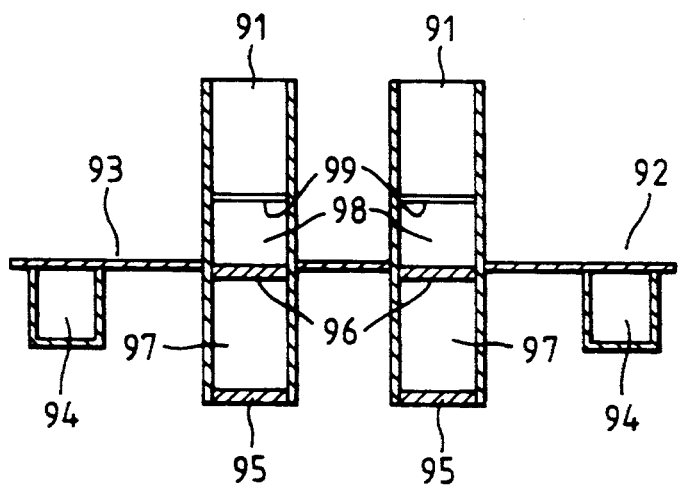

Further arrangements for suitably placing tube carriers such as those described above in a resuscitation culture medium are shown diagrammatically in FIGS. 9 and 10, which show two tube carriers 91 substantially as shown in earlier FIGS. held as a removable push fit into holes in a floatable holder 92. Holder 92 comprises a platform 93 with holes for insertion of tubes 91. Preferably platform 93 is of white plastics (rigid) sheet material for easy viewing of the condition of the media within tubes 91. Fixed around and below platform 93 is a buoyant skirt 94 filled with air or foam or other floatable material, and airtight if it relies on air flotation. Each carrier tube contains a lower (95) and upper (96) partition of porous hydrophilic polymer and a lower selective supported medium 97 and upper indicator supported medium 98. At the end of the culture period samples can be removed from the upper surfaces 99 of the upper medium.

In use, the media in the tubes can be rehydrated by contact with water and the tubes push-fitted into the holes in platform 93. Then the assembly is floated in a resuscitation medium inoculated with a sample under test and incubated. This arrangement allows the shape and size of the outer culture vessel to be varied within wide limits to accommodate various scales of resuscitation culture.

Figure 11:
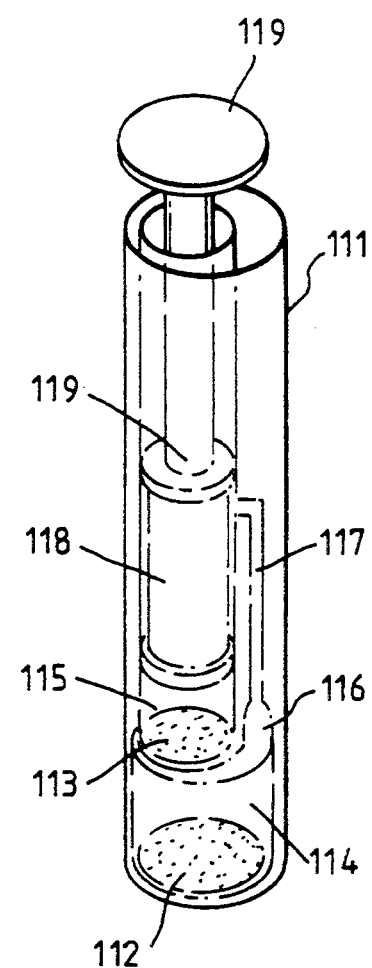
FIG. 11 shows in diagrammatic section an improved embodiment of a tube carrier for use in connection with the culture methods described herein.

An improved embodiment of a tube carrier for use in connection with the culture methods described herein is shown in FIG. 11. An injection-moulded plastics tube 111 is fitted with lower and upper partitions 112 and 113 of porous hydrophilic polymer as described above, to form a lower chamber 114 and upper chamber 115 to contain respective selective and indicator medium in use. Generally this tube carrier is provided with dry ingredients as described above in chambers 114 and 115 and distributed as a sealed sterile pack. Lower chamber 114 contacts partition 113 above, and also opens into a side bore 116–117 formed in the wall of the tube 111. Side bore 116–117 passes upwards past chamber 115 and reopens into the main bore of the tube 111 to form a vent for chamber 114. Its opening is occluded before use by a piston 118 which sealingly engages with tube 111 above chamber 115. By means of this embodiment, water for rehydration can be drawn speedily up through the lower partition 112 by pulling piston 118 up by handle 119, to rehydrate the gelled media in chambers 114 and 115. Piston 118 is removed entirely after this use and discarded, and the resulting rehydrated tube carrier can be used in a similar way to the simpler tube carriers described above, which can normally be rehydrated by simple dipping in water. This arrangement can speed up the setting up of enrichment culture according to the invention, and in use, vent 116–117 can improve the reliability of transfer of microbes from the lower to the upper chamber by venting any metabolic gas.

Other microorganisms can be resuscitated and enriched in culture using supported enrichment and/or indicator media in contact with resuscitation/growth media as indicated in accordance with this invention, by suitable substitution of appropriate media. For example, Campylobacter can be enriched and tested for by including ingredients for "Preston" selective medium (omitting the agar if desired or substituting it by an alternative gelling agent such as xanthan with lactose) in plug 47 of a version of the inserts shown in FIGS. 6 and 8, and a suitable known indicator medium in plug 49.

A useful modification that can be made to the resuscitation/growth media is to add a small amount of anti-foaming agent, for example 0.2 ml amyl alcohol in 225 ml of medium.

Although not necessary, it is possible within the scope of the invention to divide out a part of the resuscitation/growth medium which has been inoculated with sample e.g. after a period of incubation, and to use only a portion of the whole culture volume to contact the supported growth media. Thus step (c) in claim 1 can be carried out optionally after separating away a part of the culture and thereafter contacting the remainder with the supported medium or media for further incubation and culture in contact therewith, and step (d) can be modified to provide for incubation of part only of the culture produced by incubation of sample and resuscitation/growth medium to allow migration of the motile bacteria into the supported medium. In this modification of the procedure it is not necessary, but is possible, to dilute the separated portion of the resuscitation/growth culture with further medium.

At present, the inventor's preference as regards supported media for salmonella testing is for the combination of modified RV medium (lower—in direct contact with resuscitation/growth culture) and LICNR medium (upper—in contact with RV medium) in a single tube, as described above. The lower part of the tubes may if desired be masked to make the indicator reaction in the upper part more conspicuous.

Where the improved piston method of FIG. 11 is used for rehydrating the tubes of supported media, there is no need for the water-repellent coating with "RE-PLECOTE" described above as helpful for other cases. Also, when supported media carried in tubular carriers have been rehydrated, e.g. with sterile water, it can sometimes be helpful to agitate them thoroughly, e.g. using a "Whirlimixer" (trade mark).

It is within the scope of the invention to insert plural or multiple tube inserts analogous to tube 44 and its contents or other carriers of selective enrichment media, into a single specimen of resuscitation and growth medium inoculated with a sample to be tested.

In this way several possible micro-organisms can be simultaneously tested for, e.g. in the same pot.

The invention is susceptible of many modifications and variations as will be apparent to the skilled reader, and the present disclosure extends to the use of all combinations and subcombinations of the features described herein and in the accompanying drawings and claims.

I claim:

1. An article of manufacture for selectively culturing Salmonella bacteria comprising:
   a) a culture vessel containing a first liquid nutrient medium suitable for resuscitation and growth of Salmonella bacteria;
   b) a carrier comprising first and second compartments separated by a first porous partition with a pore size over 10 microns thereby to allow passage of Salmonella bacteria therethrough, said first and second compartments containing respectively a second nutrient medium and a third nutrient medium, said second and third nutrient media being selected from media suitable for bacteriologically selective growth or indication of Salmonella bacteria;
   c) said culture vessel comprising means selected from pockets, gripping formations and floats to mount said carrier so that in use said carrier partly dips into said first liquid nutrient medium within said culture vessel, said carrier having an opening below said first liquid nutrient medium surface for contact between said first liquid nutrient medium and said second nutrient medium in said first compartment of said carrier, thereby to allow migration of Salmonella bacteria from said first liquid nutrient medium into said second nutrient medium during culture of said Salmonella bacteria;
   said carrier is in the form of a tube having a central bore with a first open end and a second open end, said first open end including a second porous partition with a pore size over 10 microns thereby to allow passage of Salmonella bacteria therethrough, said first porous partition being positioned within said central bore such that said first compartment is defined by the area between said first and second partitions, said tube further includes a side bore with a first opening which operatively couples said first compartment to said central bore at a second opening which is positioned above the area occupied by the third nutrient medium contained in the second compartment for venting gas from said first compartment during culture and such that when a removable syringe piston is positioned within said central bore to draw up aqueous liquid the second opening of said side bore is occluded by said syringe piston.

2. An article of manufacture according to claim 1, wherein said second nutrient medium is a selective medium selected from gelled lysine-iron medium and gelled modified Rappaport-Vassiliadis medium, and said third nutrient medium is an indicator medium selected from brilliant green-desoxycholate medium and lysine-iron-crystine-neutral red medium, suitable for selective enrichment culture and indication of Salmonella.

3. An article of manufacture according to claim 1, wherein said second nutrient medium is a gelled medium.

4. An article of manufacture according to claim 1, wherein said second and third media are provided in the form of dry ingredients, being rehydratable to form said second and third nutrient media ready for culturing.

* * * * *